United States Patent [19]

Giret et al.

[11] Patent Number: 5,409,640

[45] Date of Patent: Apr. 25, 1995

[54] CLEANSING COMPOSITIONS

[75] Inventors: Michel J. Giret, Sunninghill; Anne Langlois, Staines; Roland P. Duke, Wokingham, all of England

[73] Assignee: The Procter & Gamble Company, Cincinnati, Ohio

[21] Appl. No.: 190,715

[22] Filed: Jan. 31, 1994

Related U.S. Application Data

[63] Continuation of Ser. No. 774,684, Oct. 11, 1991, abandoned.

[30] Foreign Application Priority Data

Oct. 12, 1990 [GB] United Kingdom ............... 9022247
Nov. 17, 1990 [GB] United Kingdom ............... 9025052
Sep. 7, 1991 [GB] United Kingdom ............... 9119162

[51] Int. Cl.$^6$ .................... C11D 1/94; C11D 3/382; C11D 17/08
[52] U.S. Cl. .................... 252/546; 252/547; 252/548; 252/174.23; 252/174.24; 252/132; 252/550; 252/554; 252/DIG. 5; 252/DIG. 13; 252/DIG. 7
[58] Field of Search ........... 252/546, 547, 548, 174.23, 252/174.24, DIG. 5, DIG. 13, DIG. 7, 132, 550, 554

[56] References Cited

U.S. PATENT DOCUMENTS

| | | | |
|---|---|---|---|
| 4,196,134 | 4/1980 | Ball et al. | 260/404.8 |
| 4,329,334 | 5/1982 | Su et al. | 252/106 |
| 4,376,789 | 3/1983 | Lowicki et al. | 424/361 |
| 4,490,355 | 12/1984 | Desai et al. | 252/DIG. 5 |
| 4,578,216 | 3/1986 | Fujii et al. | 252/542 |
| 4,654,207 | 3/1987 | Preston | 252/DIG. 13 |
| 4,673,525 | 6/1987 | Small | 252/132 |
| 4,740,367 | 4/1988 | Force et al. | 424/47 |
| 4,812,253 | 3/1989 | Small | 252/132 |

FOREIGN PATENT DOCUMENTS 0250181 12/1987 European Pat. Off. .
62-59224 3/1987 Japan .

*Primary Examiner*—Paul Lieberman
*Assistant Examiner*—Erin M. Higgins
*Attorney, Agent, or Firm*—Leonard Williamson

[57] ABSTRACT

A personal cleansing product comprising:
(a) from about 0.1% to about 20% of anionic surfactant,
(b) from about 0.1% to about 20% of amphoteric surfactant,
(c) from about 0.5% to about 25% of a vegetable oil adduct and,
(d) water.

The vegetable oil adduct can be made by Dies-Alder addition of a conjugated, elaidinized form of the vegetable oil with acrylic acid, fumaric acid or maleic anhydride. The preferred adduct is maleated soybean oil. The compositions provide excellent in-use and efficacy benefits including cleansing and lathering as well as improved mildness and skin conditioning.

12 Claims, No Drawings

CLEANSING COMPOSITIONS

This is a continuation of application Ser. No. 07/774,684, filed on Oct. 11, 1991 now abandoned.

The present invention relates to cleansing compositions. In particular it relates to foam-producing personal cleansing compositions suitable for simultaneously cleansing and conditioning the skin and/or the hair and which may be used, for example, in the form of foam bath preparations, shower products, skin cleansers, hand, face and body cleansers, shampoos, etc.

BACKGROUND OF THE INVENTION

Foaming cosmetic compositions must satisfy a number of criteria including cleansing power, foaming properties and mildness/low irritancy with respect to the skin, hair and the ocular mucosae. Skin is made up of several layers of cells which coat and protect the keratin and collagen fibrous proteins that form the skeleton of its structure. The outermost of these layers, referred to as the stratum corneum, is known to be composed of 250Å protein bundles surrounded by 80Å thick layers. Hair similarly has a protective outer coating enclosing the hair fibre which is called the cuticle. Artionic surfactants can penetrate the stratum corneum membrane and the cuticle and, by delipidization destroy membrane integrity. This interference with skin and hair protective membranes can lead to a rough skin feel and eye irritation and may eventually permit the surfactant to interact with the keratin and hair proteins creating irritation and loss of barrier and water retention functions.

Ideal cosmetic cleansers should cleanse the skin or hair gently, without defatting and/or drying the hair and skin and without irritating the ocular mucosae or leaving skin taut after frequent use. Most lathering soaps, shower and bath products, shampoos and bars fail in this respect.

Certain synthetic surfactants are known to be mild. However, a major drawback of most mild synthetic suffactant systems when formulated for shampooing or personal cleansing is poor lather performance compared to the highest shampoo and bar soap standards. Thus, surfactants that are among the mildest, such as sodium lauryl glyceryl ether sulfonate, (AGS), are marginal in lather. The use of known high sudsing anionic surfactants with lather boosters, on the other hand, can yield acceptable lather volume and quality but at the expense of clinical skin mildness. These two facts make the surfactant selection, the lather and mildness benefit formulation process a delicate balancing act.

Despite the many years of research that have been expended by the toiletries industry on personal cleansing, the broad mass of consumers remain dissatisfied by the mildness of present day cleansing compositions, finding, for example, that they have to apply a separate cosmetic lotion or cream moisturizer to the skin after using a shower or bath preparation in order to maintain skin suppleness and hydration and to counteract the delipidizing effect of the cleanser.

Thus a need exists for personal cleansing products which will produce a foam which is abundant, stable and of high quality, which are effective hair and skin cleansers, which will not dehydrate the skin or result in loss of skin suppleness, and which will provide a level of skin conditioning performance in a wash and rinse-off product which previously has only been provided by a separate post-cleansing cosmetic moisturizer.

SUMMARY OF THE INVENTION

The subject of the present invention is a foam-producing cleansing product suitable for personal cleansing of the skin or hair and which may be used as foam bath and shower products, skin cleansers and shampoos etc. According to one aspect of the invention, there is provided a personal cleansing composition comprising:

(a) from about 0.1% to about 20% of anionic surfactant, (b) from about 0.1% to about 20% of amphoteric suffactant, (c) from about 0.5% to about 25% of an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride, and (d) water, wherein the anionic surfactant and amphoteric surfactant together comprise from about 0.5% to about 30% by weight of the composition, and where the weight ratio of anionic surfactant:amphoteric surfactant is in the range from about 1:5 to about 20:1.

All concentrations and ratios herein are by weight of the cleansing composition, unless otherwise specified. Surfactant chain lengths are also on a weight average chain length basis, unless otherwise specified.

The invention relates to a foam-producing cleansing composition with superior lathering characteristics (creaminess, abundance, stability) combined with excellent mildness to the skin and hair, together with good stability, cleansing ability and conditioning performance. The invention also relates to a wash and rinse-off personal cleansing product having the above lathering, mildness and conditioning benefits.

The cleansing compositions herein are based on a combination of mild surfactants which in general terms can be selected from anionic, amphoteric, nonionic and betaine surfactants and mixtures thereof. The compositions preferably comprise a mixture of anionic and amphoteric suffactants and highly preferred systems also incorporate a nonionic or betaine surfactant. Other suitable compositions within the scope of the invention comprise mixtures of anionic with one or more nonionic or betaine surfactants or mixture thereof; and mixtures of amphoteric with one or more nonionic or betaine surfactants or mixture thereof. The level of each of the anionic and amphoteric surfactants is generally in the range from about 0.1% to about 20%, preferably from about 1% to about 15%, and especially from about 3% to about 12% by weight of the composition. The weight ratio of anionic surfactant:amphoteric surfactant, on the other hand is generally from about 1:5 to about 20:1, preferably from about 1:2 to about 5:1, and especially from about 1:1 to about 2:1. The total level of artionic and amphoteric surfactants is generally about 0.5% to about 30%, preferably from about 5% to about 25% and especially from about 10% to about 20% by weight of the cleansing composition. The nonionic or betaine surfactant, on the other hand, preferably constitutes from about 0.1% to about 20%, more preferably from about 0.1% to about 10% and especially from about 1% to about 5% by weight of the composition. The total level of surfactant, inclusive of anionic, amphoteric, nonionic, betaine and other surfactant components, is preferably from about 0.1% to about 50%, more preferably from about 6% to about 30% by weight of composition.

Anionic surfactants suitable for inclusion in the compositions of the invention can generally be described as mild synthetic detergent surfactants and include ethoxylated alkyl sulfates, alkyl glyceryl ether suffonates, methyl acyl taurates, fatty acyl glycinates, N-acyl glutamates, acyl isethionates, alkyl sulfosuccinates, alpha-sulfonated fatty acids, their salts and/or their esters, alkyl phosphate esters, ethoxylated alkyl phosphate esters, acyl sarcosinates and fatty acid/protein condensates, and mixtures thereof. Alkyl and/or acyl chain lengths for these surfactants are $C_8-C_{22}$, preferably $C_{10}-C_{18}$.

Preferred for use herein from the viewpoint of optimum mildness and lathering characteristics are the salts of sulfuric acid esters of the reaction product of 1 mole of a higher fatty alcohol and from about 1 to about 12 moles of ethylene oxide, with sodium and magnesium being the preferred counterions. Particularly preferred are the alkyl sulfates containing from about 2 to 4 moles of ethylene oxide, such as sodium laureth-2 sulfate, sodium laureth-3 sulfate and magnesium sodium laureth-3.6 sulfate. In preferred embodiments, the anionic surfactant contains at least about 50%, especially at least about 75% by weight of ethoxylated alkyl sulfate.

Preferred compositions for use herein also contain an amphoteric surfactant. Amphoteric surfactants suitable for use in the compositions of the invention include:

(a) imidazolinium surfactants of formula (II)

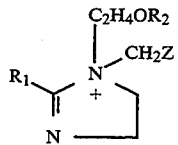

wherein $R_1$ is $C_7-C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (III)

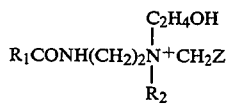

wherein $R_1$, $R_2$ and Z are as defined above;
(b) aminoalkanoates of formula (IV)

and iminodialkanoates of formula (V)

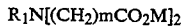

wherein n and m are numbers from 1 to 4, and $R_1$ and M are independently selected from the groups specified above; and (c) mixtures thereof.

Suitable amphoteric surfactants of type (a) are marketed under the trade name Miranol and are understood to comprise a complex mixture of species. Traditionally, the Miranols have been described as having the general formula II, although the CTFA Cosmetic Ingredient Dictionary, 3rd Edition indicates the non-cyclic structure III. In practice, a complex mixture of cyclic and non-cyclic species is likely to exist and both definitions are given here for sake of completeness. Preferred for use herein, however, are the non-cyclic species.

Examples of suitable amphoteric surfactants of type (a) include compounds of formula II and/or III in which $R_1$ is $C_8H_{17}$ (especially iso-capryl), $C_9H_{19}$ and $C_{11}H_{23}$ alkyl. Especially preferred are the compounds in which $R_1$ is $C_9H_{19}$, Z is $CO_2M$ and $R_2$ is H; the compounds in which $R_1$ is $C_{11}H_{23}$, Z is $CO_2M$ and $R_2$ is $CH_2CO_2M$; and the compounds in which $R_1$ is $C_{11}H_{23}$, Z is $CO_2M$ and $R_2$ is H.

In CTFA nomenclature, materials preferred for use in the present invention include cocoamphocarboxypropionate, cocoamphocarboxy propionic acid, and especially cocoamphoacetate and cocoamphodiacetate (otherwise referred to as cocoamphocarboxyglycinate). Specific commercial products include those sold under the trade names of Empigen CDL60 and CDR 60 (Albright & Wilson), Miranoi C2M Conc. N.P., Miranol C2M Conc. O.P., Miranol C2M SF, Miranol CM Special (Miranol, Inc.); Alkateric 2CIB (Alkaril Chemicals); Amphoterge W-2 (Lonza, Inc.); Monateric CDX-38, Monateric CSH-32 (Mona Industries); Rewoteric AM-2C (Rewo Chemical Group); and Schercotic MS-2 (Scher Chemicals).

It will be understood that a number of commercially-available amphoteric surfactants of this type are manufactured and sold in the form of electroneutral complexes with, for example, hydroxide counterions or with anionic sulfate or sulfonate surfactants, especially those of the sulfated $C_8-C_{18}$ alcohol, $C_8-C_{18}$ ethoxylated alcohol or $C_8-C_{18}$ acyl glyceride types. Preferred from the viewpoint of mildness and product stability, however, are compositions which are essentially free of (non-ethoxylated) sulfated alcohol surfactants. Note also that the concentrations and weight ratios of the amphoteric surfactants are based herein on the uncomplexed forms of the surfactants, any artionic surfactant counterions being considered as part of the overall anionic surfactant component content.

Examples of suitable amphoteric surfactants of type (b) include salts, especially the triethanolammonium salts and salts of N-lauryl-beta-amino propionic acid and N-lauryl-imino-dipropionic acid. Such materials are sold under the trade name Deriphat by General Mills and Mirataine by Miranol Inc. Amphoterics preferred for use herein, however, are those of formula II and/or III.

The compositions of the invention also contain from about 0.5% to about 25%, preferably from about 0.5% to about 15%, more preferably from about 3% to about 10% of a vegetable oil adduct which preferably has the general formula (I):

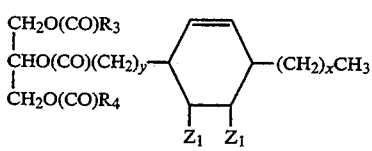

wherein x, y are integers of from 3 to 9, $R_3$ and $R_4$ are independently selected from saturated and unsaturated $C_7-C_{22}$ hydrocarbyl, each $Z_1$ is $CO_2M$ or H with at least one $Z_1$ being $CO_2M$ and wherein M is H, alkali metal, alkaline earth metal, ammonium or alkanolammonium.

Materials of this kind can generally be described as adducts prepared from vegetable oils containing non-conjugated polyunsaturated fatty acid esters which are conjugated and elaidinized then modified by Diels-Alder addition with a member of the group consisting of acrylic acid, fumaric acid and maleic anhydride. The adducts and their preparation are described in US-A-4740367, the adducts being marketed under the trade name Ceraphyl GA (Van Dyke).

Preferred vegetable oil adducts are those of Formula I prepared from soybean oil (x+y=12) and adducts derived by Diels-Alder addition of vegetable oils with fumaric acid. A preferred method of preparing adducts herein is to react two moles of vegetable oil with one mole of the dienophile in the presence of catalytic amounts of iodine, the conjugation and elaidinization agent. This produces a 50:50 blend of adduct together with disproportionated (conjugated) vegetable oil.

Preferred from the viewpoint of conditioning effectiveness in a rinse-off application are compositions in the form of oil-in-water emulsions wherein the average size of the emulsion droplets is in the range from about 1 to about 150 microns, preferably from about 20 to about 100 microns, and more preferably from about 30 to about 80 microns (droplet size being measured by, for example, laser diffraction using, e.g. a Malvern Series 2600).

The vegetable oil adduct is used herein in combination with a mild surfactant system. Suitable mild surfactants include those having a Relative Skin Barrier Penetration Value of less than about 75, preferably less than about 50 and more preferably less than about 40, Relative Skin Barrier Penetration Value being measured according to the test method set out in EP-A-0203750 (Incorporated herein by reference). Surfactants which have Relative Barrier Penetration Values of greater than 75 can be used along with the mild surfactant at low levels in the compositions of this invention, as long as their use does not significantly change the clinical skin mildness of the total cleansing composition.

Thus according to another aspect of the invention, there is provided a personal cleansing composition comprising:
(a) from about 0.1% to about 50% by weight of surfactant or mixture of surfactants having a Relative Skin Barrier Penetration Value of less than about 75,
(b) from about 0.5% to about 25% by weight of an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride.

The compositions herein preferably also contain from about 0.1% to about 20%, more preferably from about 0.1% to about 10%, and especially from about 1% to about 5% of a nonionic or betaine surfactant. Preferred herein from the viewpoint of optimum lathering and mildness are nonionic surfactants selected from $C_{12}$–$C_{14}$ fatty acid mono- and diethanolamides; alkylpolysaccharides having the general formula (VI)

$$RO(C_nH_{2n}O)_tZ_x$$

where Z is a moiety derived from glucose, fructose or galactose, R is $C_8$–$C_{18}$ alkyl or alkenyl, n is 2 or 3, t is from 0 to 10 and x is from about 1 to 10, preferably from about 1.5 to 4; polyhydroxy fatty acid amide surfactants having the general formula (VII)

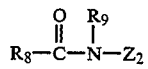

where $R_9$ is H, $C_1$–$C_4$ hydrocarbyl, 2-hydroxyethyl, 2-hydroxypropyl or a mixture thereof, $R_8$ is $C_5$–$C_{31}$ hydrocarbyl and $Z_2$ is a polyhydroxyhydrocarbyl having a linear chain with at least 3 hydroxyls directly connected to said chain, or an alkoxylated derivative thereof; or a mixture of said alkyl polysaccharide and amide surfactants.

The preferred alkyl polysaccharides herein are alkylpolyglucosides having the formula VI wherein Z is a glucose residue, R is $C_8$–$C_{18}$ alkyl or alkenyl, t is from 0 to 10, preferably 0, n is 2 or 3, preferably 2, and x is from about 1.5 to 4. In the above, x and t are understood to be weight average values and saccharide substitution is preferably at the 1-position of the saccharide. In general terms, $C_{12}$–$C_{14}$ alkyl polysaccharides are preferred from the viewpoint of lathering and $C_8$–$C_{10}$ alkyl polysaccharides from the viewpoint of skin conditioning.

To prepare these compounds, a long chain alcohol (ROH) can be reacted with glucose, in the presence of an acid catalyst to form the desired glucoside. Alternatively, the alkylpolyglucosides can be prepared by a two step procedure in which a short chain alcohol ($C_{1-6}$) is reacted with glucose or a polyglucoside (x=2 to 4) to yield a short chain alkyl glucoside (x=1 to 4) which can in turn be reacted with a longer chain alcohol (ROH) to displace the short chain alcohol and obtain the desired alkylpolyglucoside. If this two step procedure is used, the short chain alkylglucoside content of the final alkylpolyglucoside material should be less than 50%, preferably less than 10%, more preferably less than 5%, most preferably 0% of the alkylpolyglucoside.

The amount of unreacted alcohol (the free fatty alcohol content) in the desired alkylpolysaccharide surfactant is preferably less than about 2%, more preferably less than about 0.5% by weight of the total of the alkyl polysaccharide plus unreacted alcohol. The amount of alkylmonosaccharide is about 20% to about 70%, preferably 30% to 60%, more preferably 30% to 50% by weight of the total of the alkylpolysaccharide.

The preferred polyhydroxy fatty acid amide surfactants are those in which $R_9$ is $C_{1-4}$ alkyl, preferably methyl, and $R_8$ is $C_7$–$C_{19}$ alkyl or alkenyl, more preferably straight-chain $C_9$–$C_{17}$ alkyl or alkenyl, or mixture thereof; and $Z_2$ is a polyhydroxyhydrocarbyl having a linear hydrocarbyl chain with at least 3 hydroxyls directly connected to the chain, or an alkoxylated derivative (preferably ethoxylated or propoxylated) thereof, $Z_2$ preferably will be derived from a reducing sugar in a reductive amination reaction; more preferably $Z_2$ is a glycityl. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for $Z_2$. It should be understood that it is by no means intended to exclude other suitable raw materials. $Z_2$ preferably will be selected from the group consisting of —$CH_2(CHOH)_n$—$CH_2OH$, —$CH(CH_2OH)$-$(CHOH)_{n-1}$—$CH_2OH$, —$CH_2$—$(CHOH)_2(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly —CH$_2$-(CHOH)$_4$-CH$_2$OH.

The most preferred polyhydroxy fatty acid amide has the formula R$_8$(CO)N(CH$_3$)CH$_2$(CHOH)$_4$CH$_2$OH wherein R$_8$ is a C11–C17 straight chain alkyl or alkenyl group.

Betaine surfactants suitable for inclusion in the composition of the invention include alkyl betaines of the formula R$_5$R$_6$R$_7$N$^+$(CH$_2$)$_n$M (VII) and amido betaines of the formula (VIII)

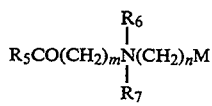

wherein R$_5$ is C$_{12}$–C$_{22}$ alkyl or alkenyl, R$_6$ and R$_7$ are independently C$_1$–C$_3$ alkyl, M is H, alkali metal, alkaline earth metal, ammonium or alkanolammonium, and n, m are each numbers from 1 to 4. Preferred betaines include cocoamidopropyldimethylcarboxymethyl betaine and laurylamidopropyldimethylcarboxymethyl betaine.

The compositions of the invention preferably also contain from about 0.5% to about 6%, preferably from about 1.5% to about 5% by weight of saturated acyl fatty acids having a weight average chain length of from 10 to 16, preferably from 12 to 14 carbon atoms. Highly preferred is myristic acid. The fatty acid is valuable both from the viewpoint of providing emolliency benefits and also for controlling the viscosity of the final composition.

The compositions of the invention preferably also contain a cationic or nonionic polymeric skin or hair conditioning agent at a level from about 0.01% to about 5%, preferably from about 0.04% to about 2% and especially from about 0.05% to about 1%. The polymer is found to be valuable for enhancing the creaminess and quality of the foam as well as providing a hair or skin conditioning utility.

Suitable polymers are high molecular weight materials (mass-average molecular weight determined, for instance, by light scattering, being generally from about 2,000 to about 3,000,000, preferably from about 5,000 to about 1,000,000).

Useful polymers are the cationic, nonionic, amphoteric, and anionic polymers useful in the cosmetic field. Preferred are cationic and nonionic polymers used in the cosmetic fields as hair or skin conditioning agents.

Representative classes of polymers include cationic and nonionic polysaccharides; cationic and nonionic homopolymers and copolymers derived from acrylic and/or methacrylic acid; cationic and nonionic cellulose resins; cationic copolymers of dimethyldiallylammonium chloride and acrylic acid; cationic homopolymers of dimethyldiallylammonium chloride; cationic polyalkylene and ethoxypolyalkylene imines; quaternized silicones, and mixtures thereof.

By way of exemplification, cationic polymers suitable for use herein include cationic guar gums such as hydroxypropyl trimethyl ammonium guar gum (d.s. of from 0.11 to 0.22) available commercially under the trade names Jaguar C-14-S(RTM) and Jaguar C-17(RTM) and also Jaguar C-16(RTM), which contains hydroxypropyl substituents (d.s. of from 0.8–1.1) in addition to the above-specified cationic groups, and quaternized cellulose ethers available commercially under the trade names Ucare Polymer JR and Celquat.

Other suitable cationic polymers are homopolymers of dimethyldiallylammonium chloride available commercially under the trade name Merquat 100, copolymers of dimethyl aminoethylmethacrylate and acrylamide, copolymers of dimethyldiallylammonium chloride and acrylamide, available commercially under the trade names Merquat 550 and Merquat S, quaternized vinyl pyrrolidone acrylate or methacrylate copolymers of amino alcohol available commercially under the trade name Gafquat, and polyalkyleneimines such as polyethylenimine and ethoxylated polyethylenimine.

Anionic polymers suitable herein include hydrophobically-modified cross-linked polymers of acrylic acid having amphipathic properties as marketed by B F Goodrich under the trade name Pemulen TR1 and Pemulen TR2; and the carboxyvinyl polymers sold by B F Goodrich under the trade mark Carbopol and which consist of polymers of acrylic acid cross-linked with polyallyl sucrose or polyallyl pentaeythritol, for example, Carbopol 934, 940 and 950.

The viscosity of the final composition (Brookfield RVT, Spindle 5, 50 rpm, 25° C.) is preferably at least about 1,000 cps, more preferably from about 2000 to about 10,000 cps, especially from about 5,000 to about 7,000 cps. Preferred compositions have non-Newtonian viscosity characteristics, however, with a viscosity (Brookfield RVT, Helipath, Spindle T-B, 5 rpm, 25° C., 1 min) in the range of from about 10,000 to about 40,000 cps, more preferably from about 20,000 to about 30,000 cps.

The cleansing compositions can optionally include a hair or skin moisturizer. The preferred level of moisturizer is from about 3% to about 40% by weight. In preferred embodiments, the moisturizer is nonocclusive and is selected from:

1. water-soluble liquid polyols;
2. essential amino acid compounds found naturally occurring in the stratum corneum of the skin; and
3. water-soluble nonpolyol nonocclusives and mixtures thereof.

Some examples of more preferred nonocclusive moisturizers are glycerin., polyethylene glycol, propylene glycol, sorbitol, polyethylene glycol and propylene glycol ethers of methyl glucose (e.g. methyl glucan-20), polyethylene glycol and propylene glycol ethers of lanolin alcohol (e.g. Solulan-75), sodium pyrrolidone carboxylic acid, lactic acid, urea, L-proline, guanidine, pyrrolidone and mixtures thereof. Of the above, glycerine is highly preferred.

Examples of other moisturizers include water-soluble hexadecyl, myristyl, isodecyl or isopropyl esters of adipic, lactic, oleic, stearic, isostearic, myristic or linoleic acids, as well as many of their corresponding alcohol esters (sodium isostearoyl-2-lactylate, sodium capryl lactylate), polyethyleneglycol esters such as PEG (6) caprylic/capryl glycerate (Softigen 767), hydrolyzed protein and other collagen-derived proteins, aloe vera gel and acetamide MEA.

A further preferred component of the compositions of the invention is a water-soluble Ca$^{2+}$/Mg$^{2+}$ sequesterant which is preferably added at a level of from about 0.1% to about 5% by weight to provide lather boosting advantages under hard water usage conditions. Suitable sequesterants include polycarboxylates, amino polycarboxylates, polyphosphates, polyphosphonates and aminopolyphosphonates such as ethylenediaminetetraacetic acid, diethylenetriamine pentaacetic acid, citric acid, gluconic acid, pyrophosphoric acid, etc. and their water-soluble salts.

A number of additional optional materials can be added to the cleansing compositions. Such materials include proteins and polypeptides and derivatives thereof; water-soluble or solubilizable preservatives such as DMDM Hydantoin, Germall 115, methyl, ethyl, propyl and butyl esters of hydroxybenzoic acid, EDTA, Euxyl (RTM) K400, Bronopol (2-bromo-2-nitropropane-1,3-diol), sodium benzoate and 2-phenoxyethanol; other moisturizing agents such as hylaronic acid, chitin, and starch-grafted sodium polyacrylates such as Sanwet (RTM) IM-1000, IM-1500 and IM-2500 available from Celanese Superabsorbent Materials, Portsmith, Va., USA and described in U.S. Pat. No. 4,076,663; solvents such as hexylene glycol and propylene glycol; low temperature phase modifiers such as ammonium ion sources (e.g. $NH_4Cl$); viscosity control agents such as magnesium sulfate and other electrolytes; colouring agents; pearlescers and opacifiers such as ethylene glycol distearate, $TiO_2$ and $TiO_2$-coated mica; perfumes and perfume solubilizers etc. Conventional nonionic emollient oils and waxes can be included as additional skin and hair conditioning agents at levels from about 0.5% to about 20%, preferably from about 0.5% to about 10%, more preferably from about 1% to about 6%. Such materials include, for example, water-insoluble silicones inclusive of non-volative polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof, mineral oils, fatty sorbitan esters (see U.S. Pat. No. 3,988,255, Seiden, issued Oct. 26th 1976), lanolin and lanolin derivatives, esters such as isopropyl myristate and triglycerides such as coconut oil and soybean oil, linoleic and linolenic acids and esters thereof, and dimer and trimer acids and esters thereof, such as diisopropyl dimerate, diisostearylmalate, diisostearyldimerate and triisostearyltrimerate. Water is also present at a level of from about 45% to about 99% preferably at least about 60% by weight of the compositions herein.

The pH of the compositions is preferably from about 4 to about 9, more preferably from about 4.5 to about 8.5, pH being controlled, for example, using a citrate buffer system.

A preferred method for preparing the composition herein comprises
a) forming an aqueous phase comprising from about 0.1% to about 50% by weight of final composition of surfactant;
b) forming a first oil phase comprising from about 0.5% to about 10% by weight of final composition of nonionic emollient oil or wax other than the vegetable oil adduct;
c) forming a second oil phase comprising from about 0.5% to about 25%, preferably from about 0.5% to about 15% by weight of final composition of the vegetable oil adduct;
d) premixing the first oil phase and the aqueous surfactant phase to form an emulsion of the first oil phase in water; and
e) thereafter admixing the second oil phase with the oil-in-water emulsion of step (d), thereby forming an emulsion of the second oil phase in the preformed oil-in-water emulsion of the first oil phase.

The invention is illustrated by the following non-limiting examples.

In the examples, all concentrations are on a 100% active basis and the abbreviations have the following designation:

| | |
|---|---|
| Amphoteric 1 | Empigen CDR 60 - an aqueous mixture of 26.5% cocoamphoacetate (the amphoteric of formula I and/or IV in which $R_1$ is coconut alkyl, $R_2$ is H, and Z is $CO_2Na$) and 1.5% cocoamphodiacetate (the amphoteric of formula I and/or IV in which $R_1$ is coconut alkyl, $R_2$ is $CH_2CO_2Na$ and Z is $CO_2Na$). |
| Amphoteric 2 | Sodium N-lauryl-beta-amino-propionate. |
| Anionic | Sodium laureth-3 sulfate |
| APG | Alkylpolysaccharide of formula VI in which R is $C_8$-$C_{10}$ alkyl, t is 0, Z is a glucose residue and x is about 1.5. |
| DEA | Coconut diethanolamide |
| MEA | Coconut monoethanolamide |
| Betaine | Cocoamidopropyldimethylcarboxymethyl betaine |
| Ceraphyl GA | Maleated soybean oil marketed by Van Dyke |
| Polymer 1 | Merquat 550 - Copolymer of acrylamide and dimethyldiallyl ammonium chloride, m.wt. $2.5 \times 10^6$ (8% solution) |
| Polymer 2 | Polymer JR-400 - hydroxyethylcellulose reacted with epichlorohydrin and quaternized with trimethylamine, m.wt. $4 \times 10^6$ |
| MA | Myristic Acid |
| Preservative | DMDM Hydantoin |
| Pearlescer | Ethyleneglycoldistearate/emulsifier mixture |
| Oil | Soyabean oil |
| Softigen 767 | PEG(6) caprylic/capryl glycerate |

EXAMPLES I to VII

The following are personal cleansing compositions in the form of shower foam products and which are representative of the present invention:

| | I | II | III | IV | V | VI | VII |
|---|---|---|---|---|---|---|---|
| Amphoteric 1 | 7.5 | 3.0 | 5.0 | 5.0 | 2.5 | 5.0 | 5.0 |
| Amphoteric 2 | — | 5.0 | 3.0 | — | 5.0 | — | — |
| Anionic | 7.5 | 9.0 | 10.0 | 10.0 | 7.5 | 10.0 | 10.0 |
| APG | 2.5 | — | 2.0 | 2.0 | — | 2.5 | 2.5 |
| DEA | 3.0 | 1.0 | — | 2.0 | 1.0 | 3.0 | — |
| MEA | — | — | — | — | — | — | 3.0 |
| Betaine | — | 2.0 | 2.0 | 1.0 | 2.5 | 2.5 | — |
| Ceraphyl GA | 5.0 | 4.0 | 6.0 | 6.0 | 5.0 | 5.0 | 5.0 |
| Polymer 1 | — | 0.1 | 0.2 | — | 0.1 | 0.2 | — |
| Polymer 2 | 0.2 | 0.1 | — | 0.2 | 0.1 | — | 0.2 |
| Softigen 767 | — | — | — | — | — | 2.0 | 1.0 |
| MA | 4.0 | 2.0 | 1.5 | 1.0 | 2.0 | 2.0 | 2.0 |
| Oil | — | — | — | — | — | 5.0 | 5.0 |
| Preservative | 0.15 | 0.15 | 0.15 | 0.15 | 0.15 | 0.2 | 0.2 |
| Pearlescer | 0.5 | — | — | 1.0 | 1.0 | 2.0 | 1.0 |
| Perfume | 1.0 17 | 1.0 | 1.0 | 1.0 | 1.0 | 1.0 | 1.0 |
| Glycerine | — | — | — | — | — | — | 3.0 |
| Water | | | | to 100 | | | |

Compositions 1 to 5 are prepared by forming a gel phase A of Polymer 1 and/or 2 in water, forming an aqueous phase B containing the remaining water-soluble, oil-insoluble ingredients, separately forming an oil phase C containing the Ceraphyl GA, MA, DEA and pearlescer, admixing phases A and B and heating to about 65°–70° C., heating phase C to about 65°–70° C. and admixing with the main mix of phases A and B, cooling to about 40°–45° C. and adding preservative, and then cooling to ambient temperature and adding the perfume. Compositions VI and VII are prepared by forming a surfactant phase A containing a portion of the water, the anionic and amphoteric surfactants and the remaining water-soluble, oil-insoluble ingredients, forming an oil phase B containing the MA, DEA, Softigen and oil, admixing B with A at about 40°–50° C., adding the remaining water, preservative and perfume and cooling to ambient temperature, and finally admixing the Ceraphyl GA. The average particle size of the emulsion droplets is about 30 micron. (Malvern Series 2600 laser diffraction).

The products provide excellent in-use and efficacy benefits including cleansing and lathering together with improved mildness and skin conditioning (hydration, suppleness etc.).

What is claimed is:

1. A personal cleansing composition comprising:
   (a) from about 3 to 12% by weight of anionic surfactant,
   (b) from about 3 to 12% by weight of amphoteric
   (c) from about 4% to about 15% by weight of an adduct prepared from vegetable oils containing non-conjugated polyunsaturated fatty acid esters which are conjugated and elaidinized and then modified via Diels-Alder addition with a member of the group consisting of acrylic acid, fumaric acid and maleic anhydride; and
   (d) water,
wherein the anionic surfactant and amphoteric surfactant together comprise from about 6% to 24% by weight of the composition, and where the weight ratio of anionic surfactant:amphoteric surfactant is in the range from about 4:1 to about 1:4; and
wherein the anionic surfactant is selected from the group consisting of ethoxylated alkyl sulfates, alkyl glyceryl ether sulfonates, methyl acyl taurates, fatty acyl glycinates, N-acyl glutamates, acyl isethionates, alkyl sulfosuccinates, alpha-sulfonated fatty acids, their salts and/or their esters, alkyl phosphate esters, ethoylated alkyl phosphate esters, acyl sarcosinates and fatty acid/protein condensates, and mixtures thereof, and
wherein the amphoteric surfactant is selected from the group consisting of
   (a) imidazolinium derivatives of formula (II)

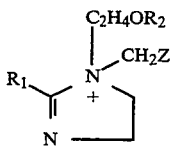

wherein $R_1$ is $C_7$–$C_{22}$ alkyl or alkenyl, $R_2$ is hydrogen or $CH_2Z$, each Z is independently $CO_2M$ or $CH_2CO_2M$, and M is H, alkali metal, alkaline earth metal, ammonium or alkanolammonium; and/or ammonium derivatives of formula (III)

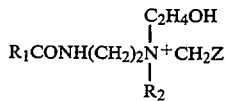

wherein $R_1$, $R_2$ and Z are as defined above:
   (b) aminoalkanoates of formula (IV)

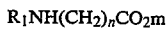

and iminodialkanoates of formula (V)

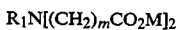

wherein n and m are numbers from 1 to 4, and $R_1$ and M are independently selected from the groups specified in (a) above; and
   (c) mixtures thereof; and
wherein said composition has a viscosity of from about 1000 cps. to about 10,000 cps and an average emulsion droplet size of 20 to about 100 microns.

2. A composition according to claim 1 additionally comprising from about 0.1% to about 10% by weight of nonionic surfactant wherein the nonionic surfactant is selected from the group consisting of alkylpolysaccharides having the general formula $RO(C_nH_{2n}O)_tZ_x$ where Z is a moiety derived from glucose, fructose or galactose, R is $C_8$–$C_{18}$ alkyl or alkenyl, n is 2 or 3, t is from 0 to 10 and x is from 1.5 to 4; polyhydroxy fatty acid amide surfactants having the formula $R_8(CO)N(R_9)Z_2$ wherein $R_9$ is H, $C_1$–$C_4$ hydrocarbyl, 2-hydroxyethyl, 2-hydroxypropyl or a mixture thereof, $R_8$ is $C_5$–$C_{31}$ hydrocarbyl and $Z_2$ is a polyhydroxyhydrocarbyl having a linear chain with at least 3 hydroxyls directly connected to said chain, or an alkoxylated derivative thereof; and mixtures of said alkyl polysaccharide and polyhydroxy fatty acid amide surfactants.

3. A composition in accordance with claim 1 wherein said composition is an emulsion having an average particle size droplet of 30 microns.

4. A composition according to claim 1 wherein the anionic surfactant comprises an ethoxylated $C_8$–$C_{b\ 22}$ alkyl sulfate.

5. A composition according to claim 1 wherein the amphoteric is selected from the group consisting of imidazolinium derivatives of formula II, ammonium derivatives of formula III, and mixtures thereof.

6. A composition according to claim 1 wherever the weight ratio of anionic surfactant:amphoteric surfactant is in the range from about 1:1 to about 2:1.

7. A composition according to claim 1 additionally comprising from about 0.5% to about 6% by weight of a saturated fatty acid having a weight-average chain length of from 10 to 16 carbon atoms.

8. A composition according to claim 1 additionally comprising from 0.01% to 5% of a cationic or nonionic polymeric skin or hair conditioning agent selected from the group consisting of cationic and nonionic polysaccharides; cationic and nonionic homopolymers and copolymers derived from acrylic and/or methacrylic acid, cationic and nonionic cellulose resins; cationic copolymers of dimethyldiallylammonium chloride and acrylic acid; cationic homopolymers of dimethyldiallylammonium chloride; cationic polyalkylene and ethoxypolyalkylene imines; quaternized silicones, and mixtures thereof.

9. A composition according to claim 6 additionally comprising moisturiser selected from the group consisting of glycerin, polyethylene glycol, propylene glycol, sorbitol, polyethylene glycol and polypropylene glycol ethers of methyl glucose, polyethylene glycol and polypropylene glycol ethers of lanolin alcohol, PEG(6) caprylic/capryl glycerate, sodium pyrrolidone carboxylic acid, lactic acid, L-proline and mixtures thereof.

10. A composition according to claim 1 additionally comprising from 0.1% to about 5% of a water-soluble $Ca^{2+}/Mg^{2+}$ sequesterant.

11. A composition according to claim 1 comprising from about 0.5% to about 20% of an additional nonionic emollient oil or wax.

12. A composition according to claim 1 wherein the vegetable oil adduct has the formula (I)

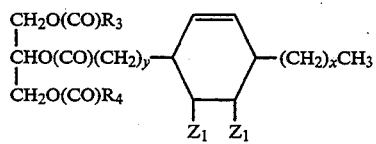
wherein x, y are integers of from 3 to 9, $R_3$ and $R_4$ are independently selected from saturated and unsaturated $C_7$–$C_{22}$ hydrocarbyl, each $Z_1$ being $CO_2M$ and wherein M is H, alkali metal, alkaline earth metal, ammonium or alkalolammonium.
* * * * *